United States Patent [19]

Tovey et al.

[11] Patent Number: 5,643,294

[45] Date of Patent: Jul. 1, 1997

[54] SURGICAL APPARATUS HAVING AN INCREASED RANGE OF OPERABILITY

[75] Inventors: H. Jonathan Tovey, Milford, Conn.; Boris Zvenyatsky, Bronx, N.Y.; Ernie Aranyi, Easton, Conn.

[73] Assignee: United States Surgical Corporation, Norwalk, Conn.

[21] Appl. No.: 623,984

[22] Filed: Mar. 28, 1996

Related U.S. Application Data

[63] Continuation of Ser. No. 270,395, Jul. 5, 1994, abandoned, which is a continuation of Ser. No. 24,579, Mar. 1, 1993, abandoned.

[51] Int. Cl.⁶ ................................................. A61B 17/28
[52] U.S. Cl. ........................ 606/148; 606/205; 606/170
[58] Field of Search .................................. 606/205, 206, 606/170, 171, 148, 51, 52, 207, 208; 128/751; 604/95; 600/146

[56] References Cited

U.S. PATENT DOCUMENTS

| 2,113,246 | 4/1938 | Wappler . |
| 3,314,431 | 4/1967 | Smith, Jr. . |
| 3,788,303 | 1/1974 | Hall . |
| 3,892,228 | 7/1975 | Mitsui . |
| 4,672,964 | 6/1987 | Dee et al. . |
| 4,688,555 | 8/1987 | Wardle . |
| 4,763,669 | 8/1988 | Jaeger . |
| 4,880,015 | 11/1989 | Nierman . |
| 4,941,455 | 7/1990 | Watanabe et al. . |
| 4,944,741 | 7/1990 | Hasson . |
| 4,947,827 | 8/1990 | Opie et al. . |
| 5,133,736 | 7/1992 | Bales et al. ................. 606/174 X |
| 5,137,013 | 8/1992 | Chiba et al. ................. 606/205 |
| 5,152,279 | 10/1992 | Wilk . |
| 5,209,747 | 5/1993 | Knoepfler . |
| 5,224,954 | 7/1993 | Watts et al. ................. 606/205 |
| 5,254,130 | 10/1993 | Poncet et al. . |
| 5,308,358 | 5/1994 | Bond et al. ................. 606/207 X |
| 5,368,606 | 11/1994 | Marlow et al. ............... 606/174 X |
| 5,439,478 | 8/1995 | Palmer ........................ 606/205 |

FOREIGN PATENT DOCUMENTS

| 69942 | 1/1983 | European Pat. Off. ........... 606/205 |
| 990220 | 1/1983 | U.S.S.R. . |

*Primary Examiner*—Michael H. Thaler

[57] ABSTRACT

A surgical instrument is provided for performing a variety of endoscopic or laproscopic procures. The instrument includes a handle assembly, a tubular body extending from the handle assembly and defining a longitudinal axis, a tool assembly associated with a distal end of the tubular body including a tool base and tool members, a first mechanism for effectuating remote articulation of the tool assembly with respect to the longitudinal axis of the tubular body, a second mechanism for effectuating remote rotation of the tool assembly about the longitudinal axis of the tubular body, and a third mechanism for effectuating remote rotation of the tool members relative to the tool base.

24 Claims, 10 Drawing Sheets

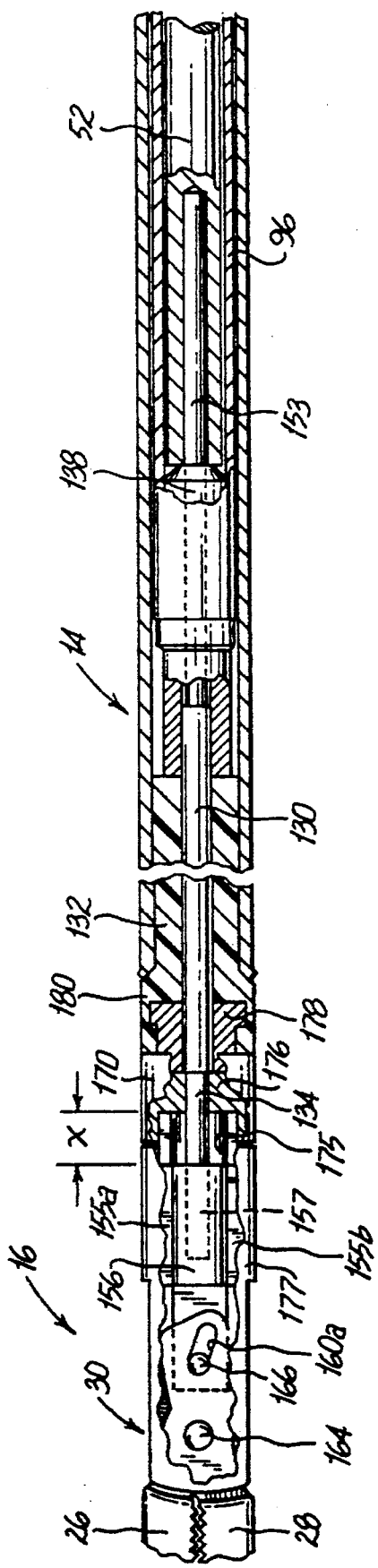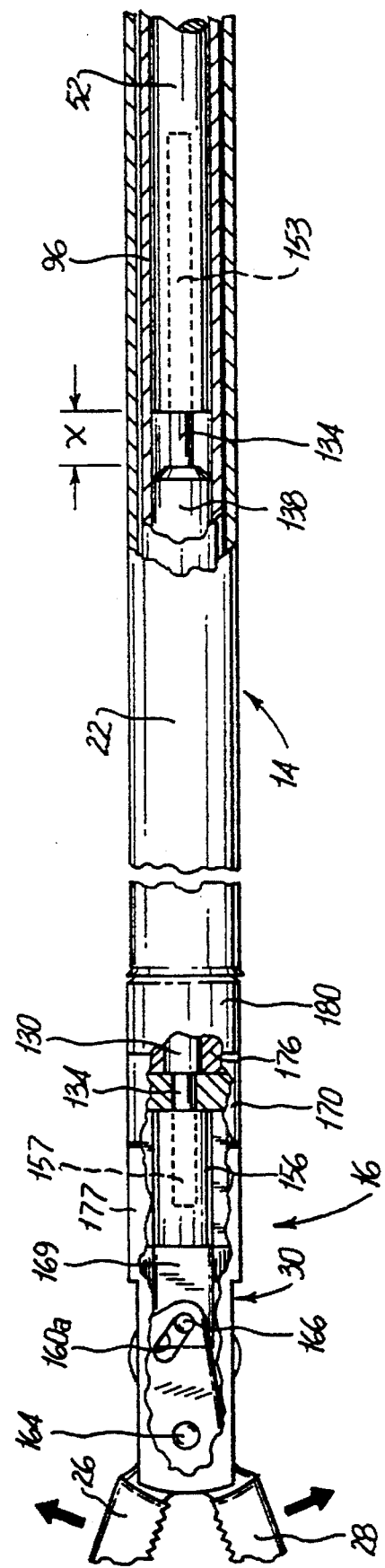

SURGICAL APPARATUS HAVING AN INCREASED RANGE OF OPERABILITY

This is a continuation of application Ser. No. 08/270,395 filed on Jul. 5, 1994, now abandoned, which is a continuation of Ser. No. 08/024,579 filed on Mar. 1, 1993 now abandoned.

BACKGROUND OF THE INVENTION

1. Field of the Invention

This invention relates to surgical apparatus, and more particularly, to an instrument for driving surgical needles during endoscopic or laparoscopic surgical procedures.

2. Description of the Related Art

In endoscopic or laparoscopic procedures, surgery is preformed through a small incision in the patient's body. The incision provides access for a trocar or cannula device which allows insertion of various surgical instruments including, for example, retractors, scissors, and clip appliers. Few instruments exist however, which are configured for insertion through a trocar or cannula device to drive surgical needles during endoscopic or laparoscopic procedures.

Needle driving instruments used in conventional surgical procedures are well known however, and include those described for example, in: U.S. Pat. No. 1,266,466 to Greeley; U.S. Pat. No. 2,795,225 to Sovatkin et al.; and U.S. Pat. No. 3,398,746 to Abramsen. Each of these patents describe hand-held needle driving instruments for performing sutured closure of tissue during procedures in which access to the surgical site is not limited to a trocar or cannula device.

An early surgical needle driver is discussed in U.S. Pat. No. 253,209 to Jones. This device comprises a handle assembly, an elongated frame extending from the handle assembly, and a pivoting jaw mechanism at the distal end of the frame for holding a surgical needle. The device disclosed in Jones is limited however, in its range of operability.

Improvements have been made in the field of surgical instrumentation to increase the range of operability of apparatus for performing surgical procedures. For example, U.S. Pat. No. 3,314,431 to Smith describes a device for insertion of an endotracheal catheter. The device includes a pivoting pilot blade which is adapted to be moved angularly through manipulation of an actuation mechanism. U.S. Pat. No. 4,880,215 to Nierman also describes an instrument having an increased range of operability. In particular, Nierman provides a biopsy forceps comprising a pivoting distal end portion which moves relative to the longitudinal axis of the instrument through actuation of a cable system. Another surgical apparatus having an increased range of operability is described in U.S. Pat. No. 4,728,020 to Green et at. This device is directed to a surgical fastener applier having a shaft assembly intermediate a proximal actuator assembly and a distal fastener applying assembly. The device provides a mechanism for rotating the shaft assembly about a first longitudinal axis. The fastener applying assembly may be manually rotated about a second transverse axis.

Other attempts at providing articulation of a distal end of a surgical instrument have made use of shape memory alloy elements such as, for example elements formed of TINEL brand material available from Raychem Corporation. Examples of uses of such material are shown in U.S. Pat. Nos. 4,665,906 and 5,067,957 to Jervis.

Currently, there is a need in the art for a needle driving instrument for use in endoscopic or laparoscopic surgical procedures which has an increased range of operability. The present invention meets these needs by providing an instrument for use in endoscopic or laparoscopic surgical procedures having a tool assembly which is adapted and configured to be articulated relative to the endoscopic body portion of the instrument, and rotated independently about an axis defined by the tool assembly to further increase the operational range of the apparatus.

These and other objects of the subject invention will become more readily apparent to those having ordinary skill in the art from the following summary of the subject invention.

SUMMARY OF THE INVENTION

Because endoscopic procedures are more common than laparoscopic procedures, the present invention shall be discussed in terms of endoscopic procedures and apparatus. However, use herein of terms such as "endoscopic", "endoscopically", and "endoscopic portion", among others, should not be construed to limit the present invention to an apparatus for use only in conjunction with an endoscopic tube. To the contrary, it is believed that the present invention may find use in procedures wherein access is limited to a small incision including but not limited to laparoscopic procedures.

A novel surgical apparatus having an increased range of operability is provided for driving surgical needles during endoscopic or laparoscopic procedures. The apparatus comprises a handle assembly, an elongated body portion extending from the handle assembly and defining a longitudinal axis, and a tool assembly associated with a distal end portion of the elongated body portion. The tool assembly includes a tool base portion and independently rotatable tool means. The surgical apparatus of the subject invention further comprises means for effectuating remote articulation of the tool assembly between a first position substantially parallel to the longitudinal axis of the elongated body portion and at least a second position disposed angularly with respect to the longitudinal axis of the elongated body portion. Means are also provided for effectuating remote rotation of the tool assembly about the longitudinal axis of the elongated body portion of the instrument relative to the handle assembly, and means are provided for effectuating remote rotation of the tool means relative to the tool base portion to further increase the range of operability of the instrument.

The means for effectuating the remote articulation of the tool assembly preferably comprises a resilient articulation member which interconnects the tool assembly to the distal end of the elongated body portion of the instrument. Preferably, the resilient articulation member is formed of a shape memory alloy having a preformed angular configuration adapted to be moved from a stressed position substantially parallel with the longitudinal axis defined by the elongated body portion of the instrument to an unstressed position disposed substantially angularly with respect to the longitudinal axis defined by the elongated body portion of the instrument. Preferably, the articulated movement of the articulation member is achieved through longitudinal movement of an elongated cam tube which translates reciprocatingly with respect to the resilient articulation member. The longitudinal translation of the cam tube is preferably achieved through operation of an axial drive screw assembly which includes a rotator sleeve threadably engaged about an axially movable driving screw. The driving screw is connected at the distal end portion thereof to the elongated cam tube such that rotation of the sleeve will cause corresponding longitudinal translation of the cam tube to articulate the tool assembly between a first substantially position and the second angularly disposed position.

The means for effectuating the remote rotation of the tool assembly relative to the longitudinal axis of the elongated body portion of the instrument preferably comprises an annular dial member which is positioned in the barrel portion of the handle assembly and which is coaxially engaged about an elongated rotator tube. The rotator tube extends longitudinally through the elongated cam tube to the tool base of the tool assembly such that rotation of the dial member results in corresponding rotation of the entire tool assembly relative to the longitudinal axis of the elongated body portion of the apparatus.

The means for effectuating the independent remote rotation of the tool means relative to the tool base portion of the tool assembly preferably comprises a rotation knob associated with the barrel portion of the handle assembly, and an elongated rotator rod extending from the rotation knob, through the rotator tube, to the tool means. Rotation of the rotator knob will cause corresponding rotation of the tool means with respect to the tool base portion to further increase the range of operability of the surgical apparatus of the subject invention.

Preferably, the tool means of the surgical apparatus of the subject invention comprises a pair of cooperating jaw members which are configured and adapted for holding a surgical needle, although other tool structures are envisioned including, for example, retractor blades, forceps, or graspers. In the preferred embodiment of the subject invention, the needle holding jaw members are remotely actuated through control means extending from the handle assembly which move the cooperating jaw members between an open position to receive a surgical needle and a closed position to securely hold a surgical needle. Jaw actuation is achieved by causing reciprocating longitudinal movement of the elongated rotator rod through manipulation of a pivoting handle associated with the handle assembly of the instrument. The longitudinal translation of the rotator rod is transmitted to the cooperating jaw members by a control wire which extends through the resilient articulator tube.

Further features of the needle driving apparatus of the subject invention will become more readily apparent from the following detailed description of the instrument taken in conjunction with the drawings.

BRIEF DESCRIPTION OF THE DRAWINGS

The needle driving apparatus of the subject invention will be described hereinbelow with respect to the drawings wherein:

FIG. 8A is a side elevational view of the needle holding jaws illustrated in FIG. 8 in a first independently rotated position;

FIG. 8B is a side elevational view of the needle holding jaws illustrated in FIG. 8 in a second independently rotated position;

FIG. 11 is a side elevational view in partial cross-section of the endoscopic portion and the needle holding assembly of the apparatus of FIG. 1 illustrating the needle holding jaws thereof in a closed position; and FIG. 12 is a side elevational view in partial cross-section of the endoscopic portion and the needle holding assembly of the apparatus of FIG. 1 illustrating the needle holding jaws thereof in an open position.

DETAILED DESCRIPTION OF THE PREFERRED EMBODIMENTS

Figure 1:
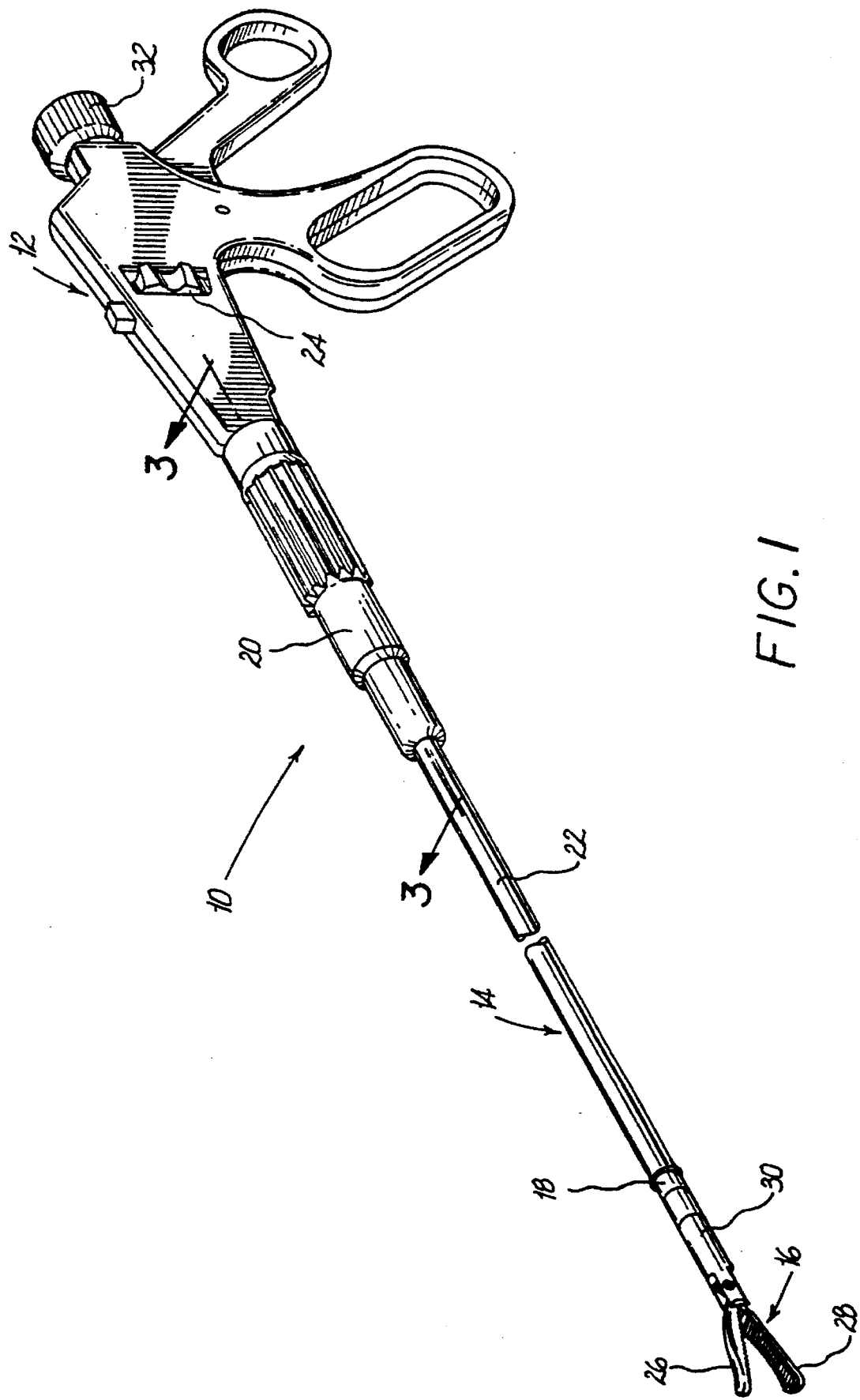
FIG. 1 is a perspective view of a needle driving apparatus in accordance with a preferred embodiment of the subject invention.

In the drawings and in the description which follows, the term "proximal", as is traditional, will refer to the end of the surgical apparatus of the subject invention which is closest to the operator, while the term "distal" will refer to the end of the apparatus which is furthest from the operator.

The surgical apparatus of the subject invention is illustrated in FIG. 1 and designated generally by reference numeral 10. In the present preferred embodiment, the surgical apparatus 10 has been configured for driving surgical needles. It is contemplated however, that a wide variety of tool means may be used with this apparatus including, but not limited to, graspers, retractors, forceps, clamps, etc. Surgical apparatus 10 is configured for suturing tissue during endoscopic or laparoscopic procedures in which access to the surgical site is limited to a trocar or cannula device. In brief, the needle driving apparatus 10 of this embodiment of the subject invention comprises a handle assembly 12, an elongated tubular body portion 14 extending longitudinally from the handle assembly 12 and preferably dimensioned for endoscopic utilization, and a tool assembly 16 operatively associated with the distal end 18 of the elongated body portion 14.

The surgical apparatus 10 of the subject invention is particularly adapted to provide the user with an increased range of operability to perform a surgical task, such as, for example, driving a surgical needle to suture body tissue during an endoscopic procedure. The increased range of operability of surgical apparatus 10 is achieved through a plurality of mechanisms, each functioning to move the tool assembly 16 of the instrument within a distinct rotational and/or angular plane of motion. One of the mechanisms for effectuating movement of tool assembly 16 functions to articulate the tool assembly 16 into an angularly disposed position with respect to the longitudinal axis of elongated body portion 14. This first mechanism includes an axial driving screw assembly 20 which causes translation of an elongated cam tube 22. Another mechanism is provided for effectuating the remote rotation of the tool assembly 16 about the longitudinal axis of elongated body portion 14. This second mechanism includes a medial rotator dial 24 operatively associated with handle assembly 12. Still another mechanism is provided for effectuating the remote rotation of the needle holding jaw members 26 and 28 of tool assembly 16 relative to the base of the clevis portion 30 in which they are housed. This third mechanism includes a proximal rotator knob 32 associated with the handle assembly 12. Each of these mechanisms, which function to increase the range of operability of the endoscopic needle driving apparatus 10 of the subject invention, will be discussed in greater detail hereinbelow.

Figure 2:
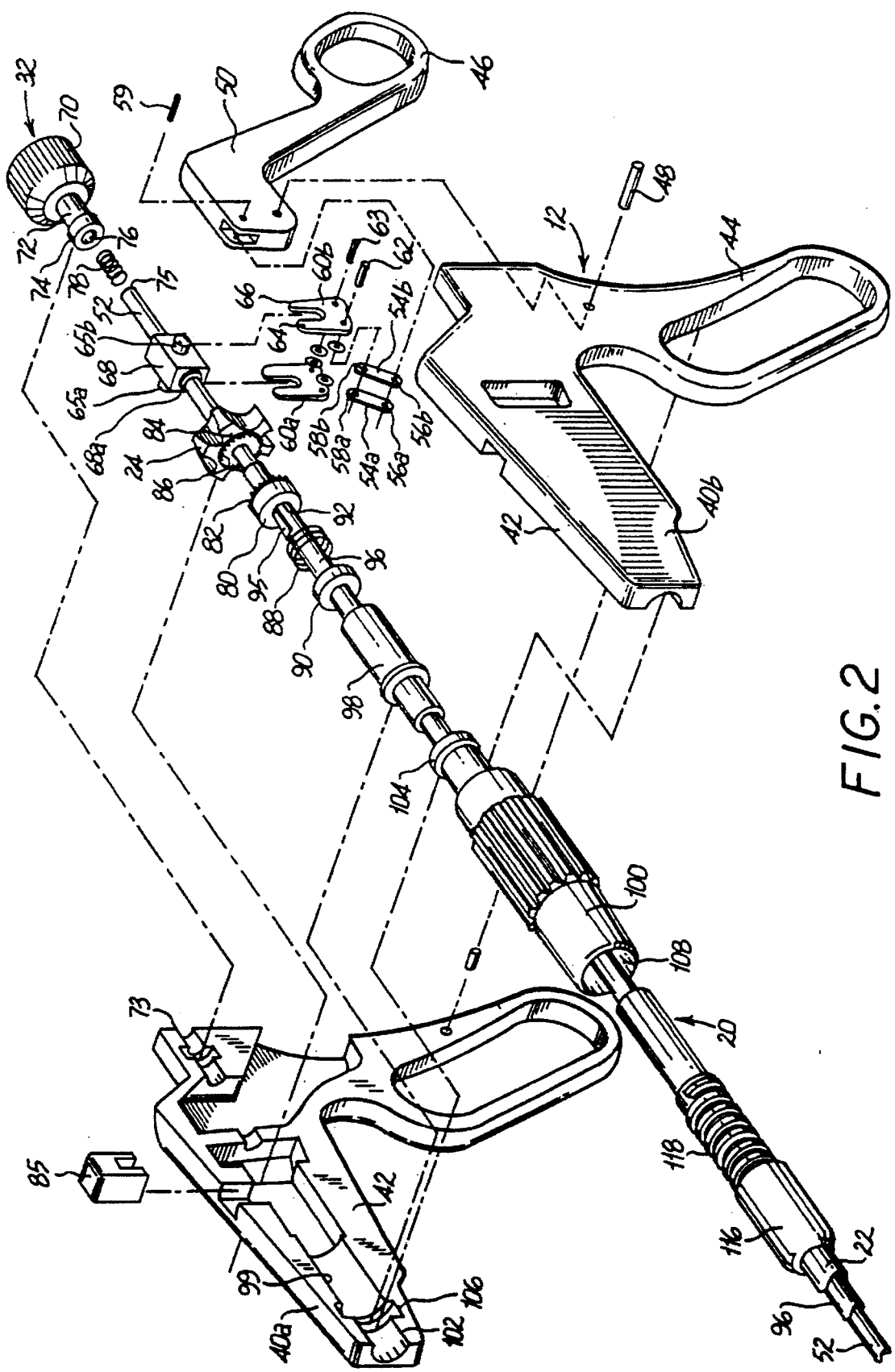
FIG. 2 is an exploded perspective view of the handle assembly of the needle driving apparatus of FIG. 1.

Referring now to FIG. 2, the handle assembly 12 of the surgical apparatus 10 of the subject invention comprises right and left hemi-portions 40a and 40b, preferably formed of a durable light-weight plastic material, such as, for example, LEXAN brand material which is manufactured by General Electric Corporation. The right and left hemi-sections 40a and 40b may be mounted to one another through any known means of affixation including, for example, sonic welding or gluing. Once assembled, the handle assembly 12 defines a barrel portion 42, a fixed gripping handle 44, and pivoting handle member 46. Pivoting handle 46 is mounted adjacent barrel portion 42 by pivot pin 48. A linkage mechanism is associated with the shank portion 50 of pivoting handle 46 for operatively interacting with a central control rod 52. The linkage mechanism includes dual interlink members 54a and 54b pinned at respective lower ends 56a and 56b thereof to pivoting handle 46 by means of a pin 59, and at respective upper ends 58a and 58b thereof to forked engaging links 60a and 60b by means of a pin 62. Engaging links 60a and 60b are connected to one another by pin 63 and are each configured with a pair of upright fingers 64 and 66 for reception of opposed transverse engaging bosses 65a and 65b which are associated with a rod coupling block 68. Rod coupling block 68 is configured to coaxially receive and mount the central control rod 52 such that manipulation of pivoting handle 46 causes corresponding longitudinal translation of the central control rod 52 through interaction of the linkage mechanism with transverse engaging pin 65b (see FIG. 10). In particular, the longitudinal movement of control rod 52 by coupling block 68 is achieved through the provision of a distal retaining ring 68a which has a fixed longitudinal position with respect to control rod 52 while permitting rotation of control rod 52 with respect thereto. The longitudinal translation of control rod 52 effectuates actuation of the cooperating jaw members 26 and 28 of tool assembly 16, as will be discussed in greater detail hereinbelow.

The mechanism for independently effectuating the remote rotation of the cooperating needle holding jaws 26 and 28 with respect to the base of tool assembly 16 includes, as discussed briefly above, rotation knob 32 which is defined by a cylindrical manipulator portion 70 adapted and configured for manual rotation by the user. A mounting portion 72 having an annular flange 74 extends from manipulator portion 70 for engagement in a proximal bore 73 formed in the barrel portion 42 of handle assembly 12. An axial bore 76 extends proximally into rotator knob 32 for receiving the proximal end 75 of central control rod 52. Axial bore 76 is particularly dimensioned to permit longitudinal translation of control rod 52 in a proximal direction when the pivoting handle 46 of handle assembly 12 is compressed to actuate the needle holding jaw members 26 and 28 of tool assembly 16. In addition, a biasing spring 78 is provided in axial bore 76, adjacent the proximal end 75 of control rod 52, to effectuate the return of control rod 52 in a distal direction upon release of pivoting handle 46 by the user. In use, axial rotation of rotator knob 32 will cause the corresponding rotation of control rod 52, which in turn, will be translated through the elongated body portion 14 of surgical apparatus 10 to the jaw members 26 and 28 to effectuate their rotation relative to the base of tool assembly 16 (see FIG. 8). The specific operational relationship between jaw members 26 and 28 and the base of tool assembly 16 will be discussed in greater detail hereinbelow.

The mechanism for effectuating the remote rotation of the entire tool assembly 16, including the jaw members 26 and 28, and the clevis portion 30 which houses and/or supports the jaw members, comprises the rotator dial 24 discussed briefly above, and a rotator assembly associated with the barrel portion 42 of handle assembly 12. The rotator assembly is adapted to be selectively locked by the user though operation of a frictional locking member 85 and includes a ratchet bushing 80 having a plurality of rearwardly projecting ratchet teeth 82 configured for ratcheting interaction with corresponding forwardly extending ratchet teeth 84 defined on an inner race surface 86 of rotator dial 24. A coiled biasing spring 88, which is positioned proximal to a spring retention ring 90, urges ratchet bushing 80 into operative contact with the inner race surface 86 of rotator dial 24 to interengage the respective ratchet teeth. An axial passage 92 extends through ratchet bushing 80 to lockingly engage and retain the proximal end 94 of an elongated rotator tube 96 by means of a key connection 95. Rotator tube 96 extends operatively from the barrel portion 42 via a spacer tube 98 disposed in an axial chamber 99 defined therein, through the elongated body portion 14 of the needle driving apparatus 10, to the tool assembly 16 which is associated with the distal end 18 thereof. In use, axial rotation of dial member 24 will cause corresponding rotation of rotator tube 96 to effectuate remote rotation of the tool assembly 16 about the longitudinal axis defined by the elongated body portion 14 of surgical apparatus 10, thereby increasing the range of operability of the instrument (see FIG. 7).

Figure 3:
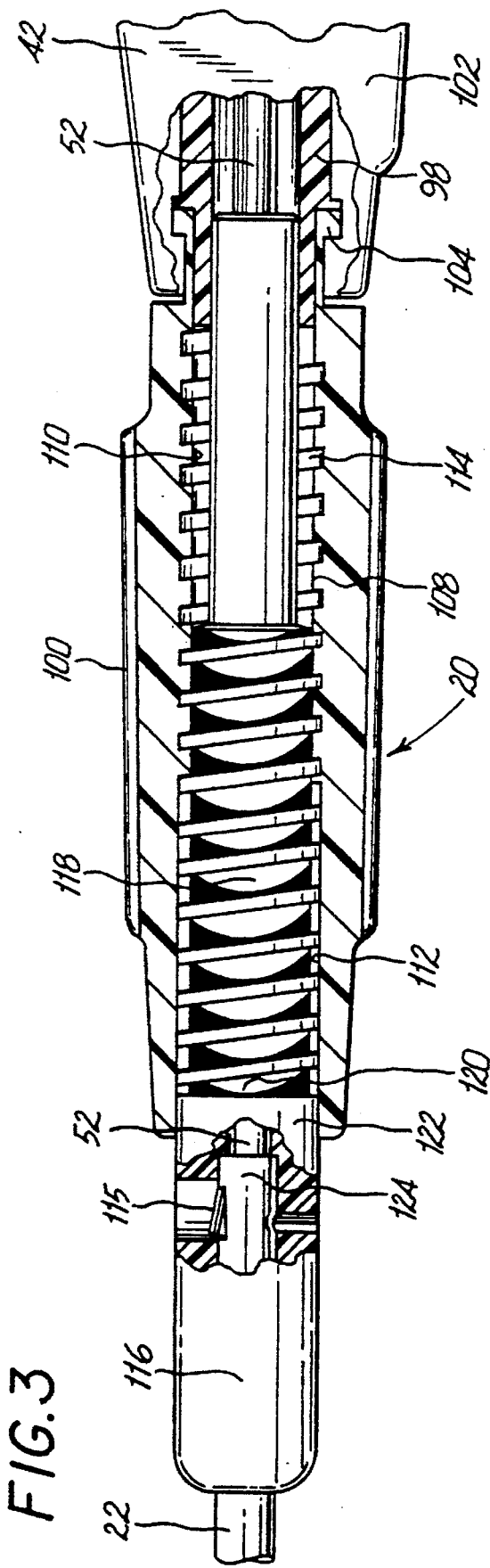
FIG. 3 is a side cross-sectional view taken along line 3—3 of FIG. 1 illustrating the distal-most position of the drive screw which effectuates the articulation of the needle holding assembly thereof.
Figure 4:
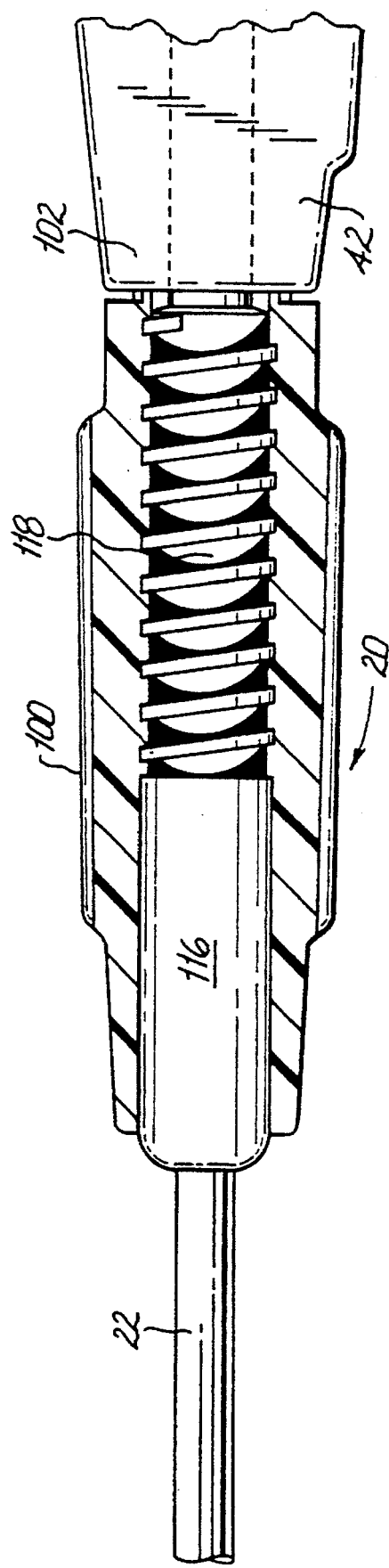
FIG. 4 is a side cross-sectional view taken along line 4—4 of FIG. 6 illustrating the proximal-most position of the drive screw which effectuates the articulation of the needle holding assembly thereof.

Turning now to FIGS. 3 and 4 in conjunction with FIG. 2, the mechanism for effectuating the articulation of the tool assembly 16 within an angular sector of rotation, preferably extending through 90°, includes a driving screw assembly 20 including an elongated manipulator sleeve 100 mounted for rotational movement relative to the distal end 102 of barrel portion 42. The mounting of manipulator sleeve 100 is achieved through an annular flange 104 retained in a correspondingly dimensioned annular chamber 106 formed adjacent the distal end 102 of barrel portion 42. A stepped axial bore 108 extends through manipulator sleeve 100 and defines a proximal region 110 and a distal region 112. Proximal region 110 is formed with an internally threaded area 114, while the distal region 112 is dimensioned for housing a translating cylindrical drive member 116. A threaded drive screw 118 is disposed substantially within the proximal region 110 of stepped axial bore 108 and is adapted and configured for travelling in an axial direction in response to rotation of the internally threaded manipulator sleeve 100.

The distal end 120 of drive screw 118 is connectively engaged to the proximal end 122 of the cylindrical drive member 116, while the proximal end 124 of the elongated cam tube 22 is engagably retained in an axial passageway 126 extending through the cylindrical drive member 116 by a lance connection 115. Thus, progressive rotation of manipulator sleeve 100 will cause corresponding longitudinal movement of drive member 116 through translation of threaded drive screw 118 to reciprocate cam tube 22 between a proximal position and a distal position, resulting in the tool assembly 16 being articulated within a 90° angular sector (see FIG. 6).

Figure 5:
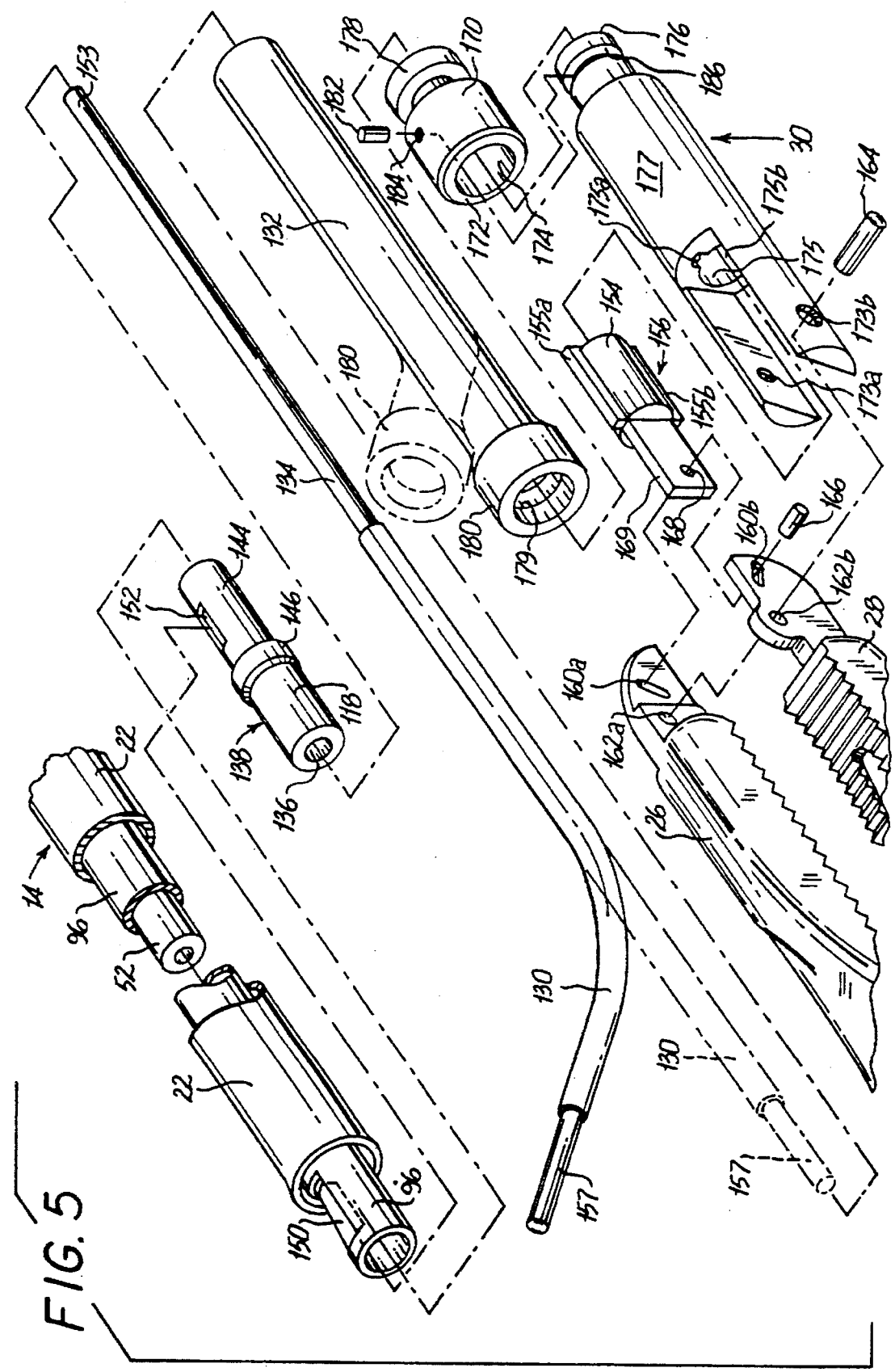
FIG. 5 is an exploded perspective view of the endoscopic portion and the needle holding assembly of the needle driving apparatus of FIG. 1.

Referring to FIG. 5, in particular, articulation of the distal end of surgical instrument 10 is achieved by an articulator tube 130 which is preferably formed of a resilient shape memory alloy. An example of a shape memory alloy suitable for this application is TINEL brand material which is available from Raychem Corporation. This material is comprised of a composition of nickel and titanium which can be formed into a structural element the configuration of which can be controlled mechanically by application of external stress. In the present embodiment of the subject invention, the preformed unstressed shape of articulator tube 130 is a 90° elbow configuration. Thus, when a stress is applied to the 90° articulator tube 130 by longitudinal movement of the elongated cam tube 22 in a distal direction in response to manipulation of sleeve 100, articulator tube 130 will gradually conform to a substantially elongated longitudinal position as it becomes progressively enclosed within the axially passageway of cam tube 22. The provision of elbow configurations of other unstressed angles is within the scope of the present invention and may be dictated by the needs of the surgeon.

Articulator tube 130 extends coaxially through a flexible tube housing 132 which interconnects the distal end 18 of endoscopic portion 14 to the tool assembly 16. Tube housing 132 is preferably fabricated from a material which is sufficiently tractable to comply with the resilient forces exerted by the articulator tube 130 as it relaxes from its stressed condition. An example of a material which conforms to these specifications is a plastic material such as, for example, polyurethane. Articulator tube 130 permits coaxial passage of an actuation wire 134 which is associated with the cooperative movement of the needle holding jaws 26 and 28 (see FIGS. 11 and 12). The proximal end of articulator tube 130 is fixedly mounted within a cavity 136 which is defined in the distal end portion of an adaptor shaft 138, while the distal end of articulator tube 130 extends into the clevis portion 30 of tool assembly 16 wherein it is mounted.

Adaptor shaft 138 is defined by a proximal engaging portion 144, a medial flange portion 146, and a distal engaging portion 148. Proximal engaging portion 144 is fixedly engaged in the distal end of rotator tube 96 by means of a depending projection 150 which engages a slot 152 in adaptor shaft 138. The distal engaging portion 148 of adaptor shaft 138 serves to coaxially support the proximal end 153 of actuation wire 134 which is operatively associated with the cooperating needle holding jaws 26 and 28. The distal end 157 of actuation wire 134 is terminated in a piston member 156 which moves reciprocatingly in a longitudinal direction in response to manipulation of pivoting handle 46 to operate jaw members 26 and 28.

With continuing reference to FIG. 5, each of the needle holding jaws 26 and 28 of tool assembly 16 is provided respectively with an angled cam slot 160a and 160b and a pivot aperture 162a and 162b. The pivot apertures 162a and 162b function to receive a pivot pin 164, while the oppositely angled cam slots 160a and 160b function to receive a translating cam pin 166. Cam pin 166 also extends through an aperture 168 provided in the rectangular distal portion 169 of piston member 156 to establish the operational connection between the piston 156 and the jaws 26 and 28. The proximal body portion 154 of piston member 156 is provided with diametrically opposed outwardly extending ribs 155a and 155b which are dimensioned and configured for translation within corresponding diametrically disposed tracks 175a and 175b formed in the axial passageway 175 which extends through the body 177 of clevis member 30. The positioning of ribs 155a and 155b of piston member 156 in corresponding tracks 175a and 175b of clevis member 30 functions to fix the angular orientation of piston member 156 with respect to clevis member 30 to facilitate the independent rotation of the needle holding jaws 26 and 28 relative to the base of tool assembly 16. In use, manipulation of pivoting handle 46 as described hereinabove, will cause corresponding longitudinal translation of central control rod 52, resulting in the axial movement of actuation wire 134 which moves piston member 156 longitudinally. At such a time, cam pin 166 will translate within the respective angled cam slots 160a and 160b of jaw members 26 and 28 causing their cooperative movement between a needle receiving position and a needle holding position.

Tool assembly 16 includes clevis member 30 which functions to operatively house jaw members 26 and 28 by means of pivot pin 164 mounted through opposed apertures 173a and 173b, and a chuck member 170 which is adapted to be mounted in the distal end 180 of the flexible tube housing 132. In particular, chuck member 170 defines a cylindrical distal portion 172 having an axial bore 174 dimensioned for reception of the proximal engaging portion 176 of clevis member 30, and an annular mounting portion 178 dimensioned for reception in an annular slot 179 formed within the distal end 180 of flexible housing tube 132. A set pin 182 extends through an aperture 184 provided in the distal portion 172 of chuck member 170 and into an annular groove 186 formed in the proximal engaging portion 176 of clevis member 30 which serves to fix the longitudinal position of clevis member 30 and chuck member 170 while permitting the relative rotation of clevis member 30 with respect to chuck member 170. Thus, in use, manual rotation of knob member 32 will transmit rotational motion through control rod 52 and actuation wire 134 to piston member 156 which will rotate clevis member 30, together with jaws 26 and 28, relative to chuck member 170, thereby further increasing the operational range of the needle driving instrument 10 of the subject invention. It is envisioned that chuck member 170 may be formed integral with the distal end 180 of flexible housing tube 132, whereby clevis member 30 would be mounted directly to housing tube 132 by means of set pin 182.

In operation, to introduce the apparatus 10 of the subject invention into the abdominal cavity of a patient during an endoscopic procedure, the tool assembly 16 should be aligned with the longitudinal axis defined by the elongated body portion 14 of the instrument, as illustrated in FIG. 1, to facilitate its insertion through an opening or a trocar or cannula device. Once the apparatus has been extended into the patient's abdominal cavity, the surgeon may increase the operational range of the instrument by articulating the tool assembly 16 with respect to the elongated body portion 14 thereof.

Figure 6:
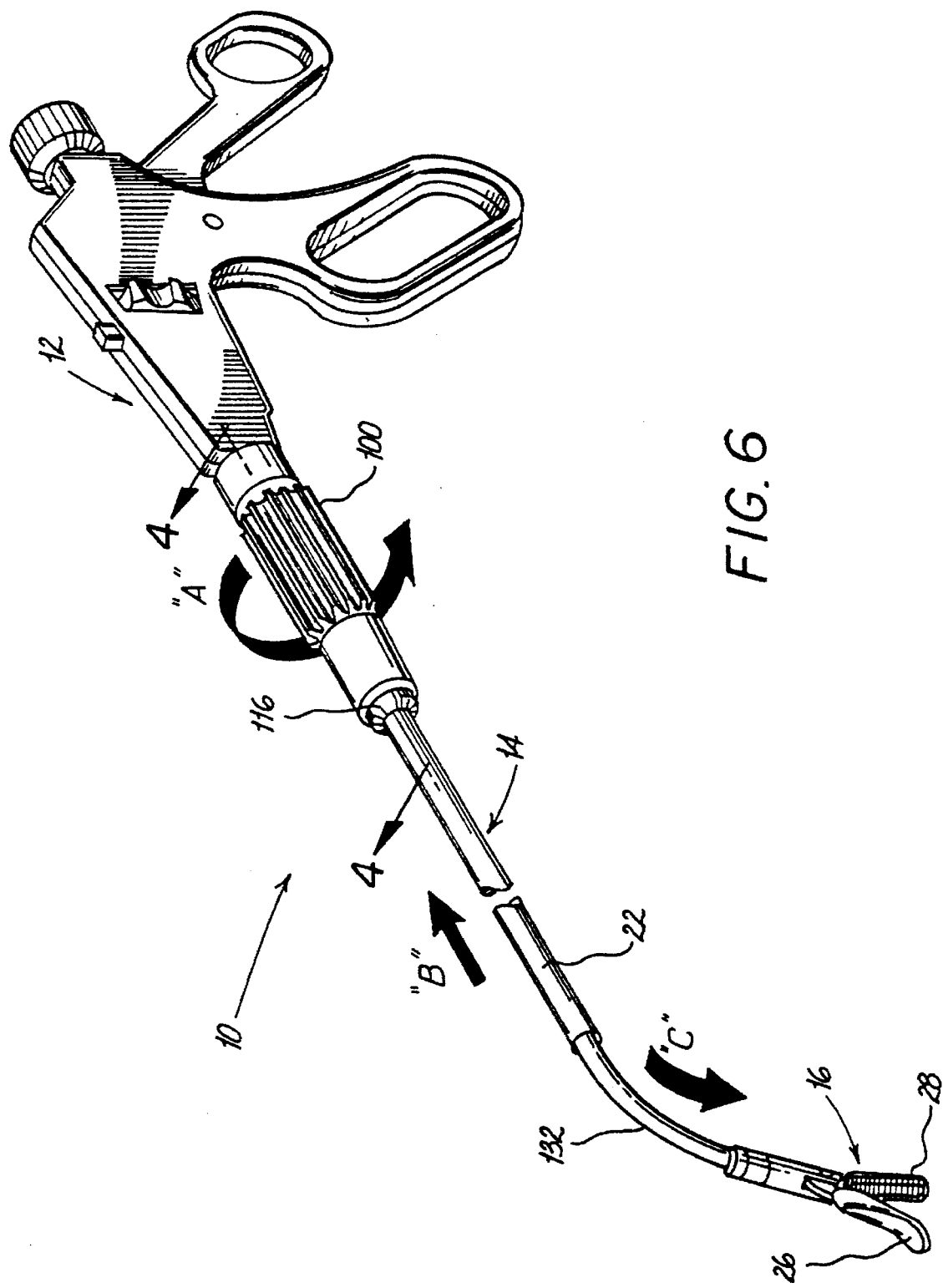
FIG. 6 is a perspective view of the needle driving apparatus of FIG. 1 with the needle holding assembly thereof disposed in an articulated position.

With additional reference to FIG. 6, progressive articulation of tool assembly 16 with respect to the longitudinal axis of elongated body portion 14 is achieved by rotating the manipulator sleeve 100 in the direction indicated by arrow "A". At such a time, the elongated cam tube 22 is drawn proximally as indicated by arrow "B" as the cylindrical drive member 116 is pulled rearwardly by driving screw 118. The proximal retreat of cam tube 22 permits the resilient articulator tube 130 to relax from its stressed condition urging the flexible housing tube 132 to comply along the angular path indicated by arrow "C". The degree of articulation can be varied within a 90° angular sector as desired by the surgeon. Once articulated into a desirable position, the surgeon may further increase the operational range of the apparatus by rotating the entire tool assembly 16 about the longitudinal axis of the elongated body portion 14.

Figure 7:
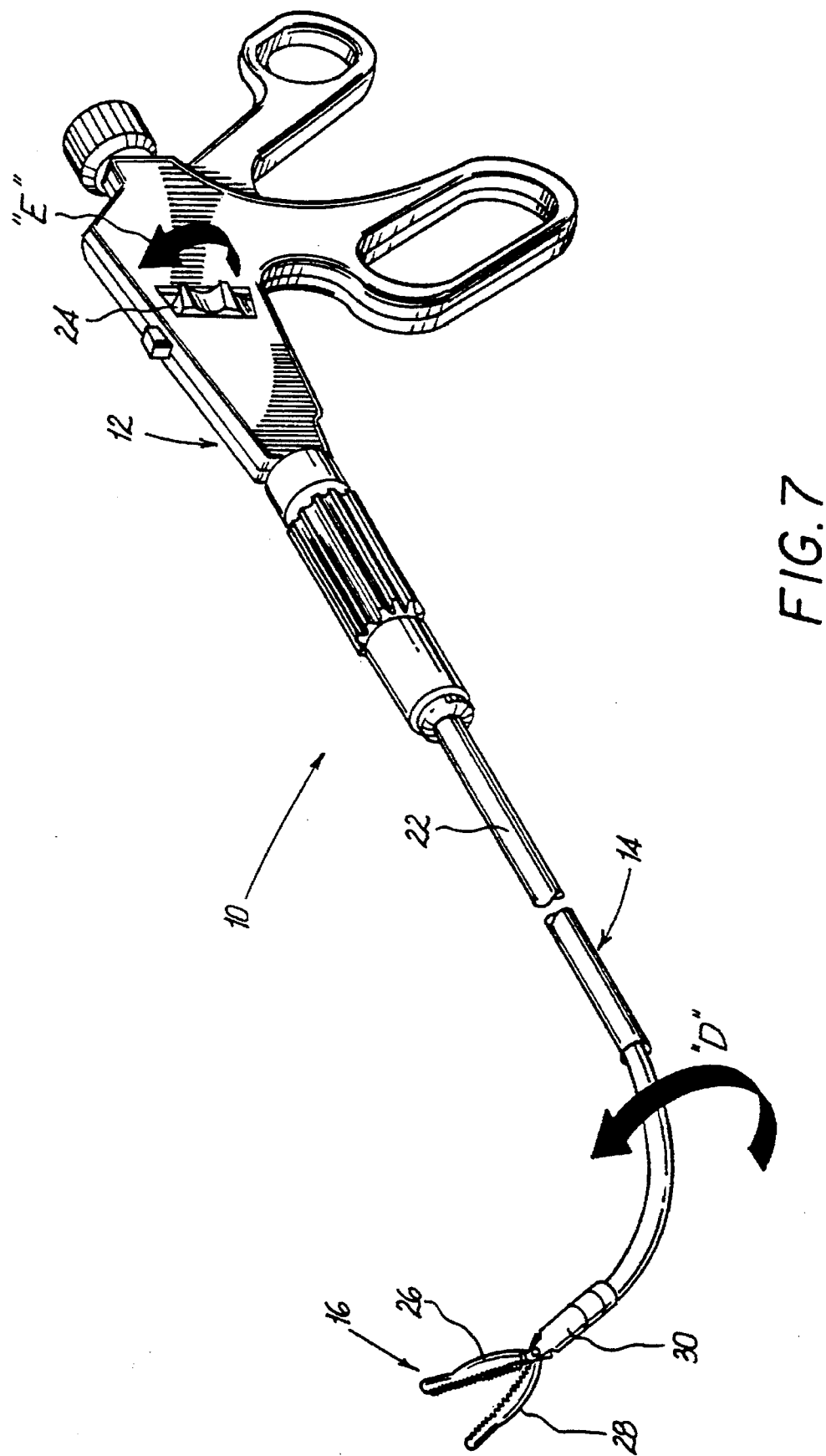
FIG. 7 is a perspective view of the needle driving apparatus of FIG. 1 illustrating the rotation of the articulated needle holding assembly about the longitudinal axis of the endoscopic portion of the instrument.

Referring to FIG. 7, rotation of the entire tool assembly 16 about the longitudinal axis of elongated body portion 14 as indicated by directional arrow "D" is achieved through manual rotation of rotator dial 24 as indicated by directional arrow "E". Moreover, progressive rotation of dial 24 in a clockwise direction will effectuate remote rotation of tool assembly 16 in a clockwise direction, while progressive rotation of dial 24 in a counter-clockwise direction will effectuate remote rotation of tool assembly 16 in a counter-clockwise direction. Once the surgeon has rotated the entire tool assembly 16 into a desired position, the operation range of the apparatus may be increased even further by effectuating the independent rotation of the needle holding jaws 26 and 28 with respect to the base of tool assembly 16.

Figure 8:
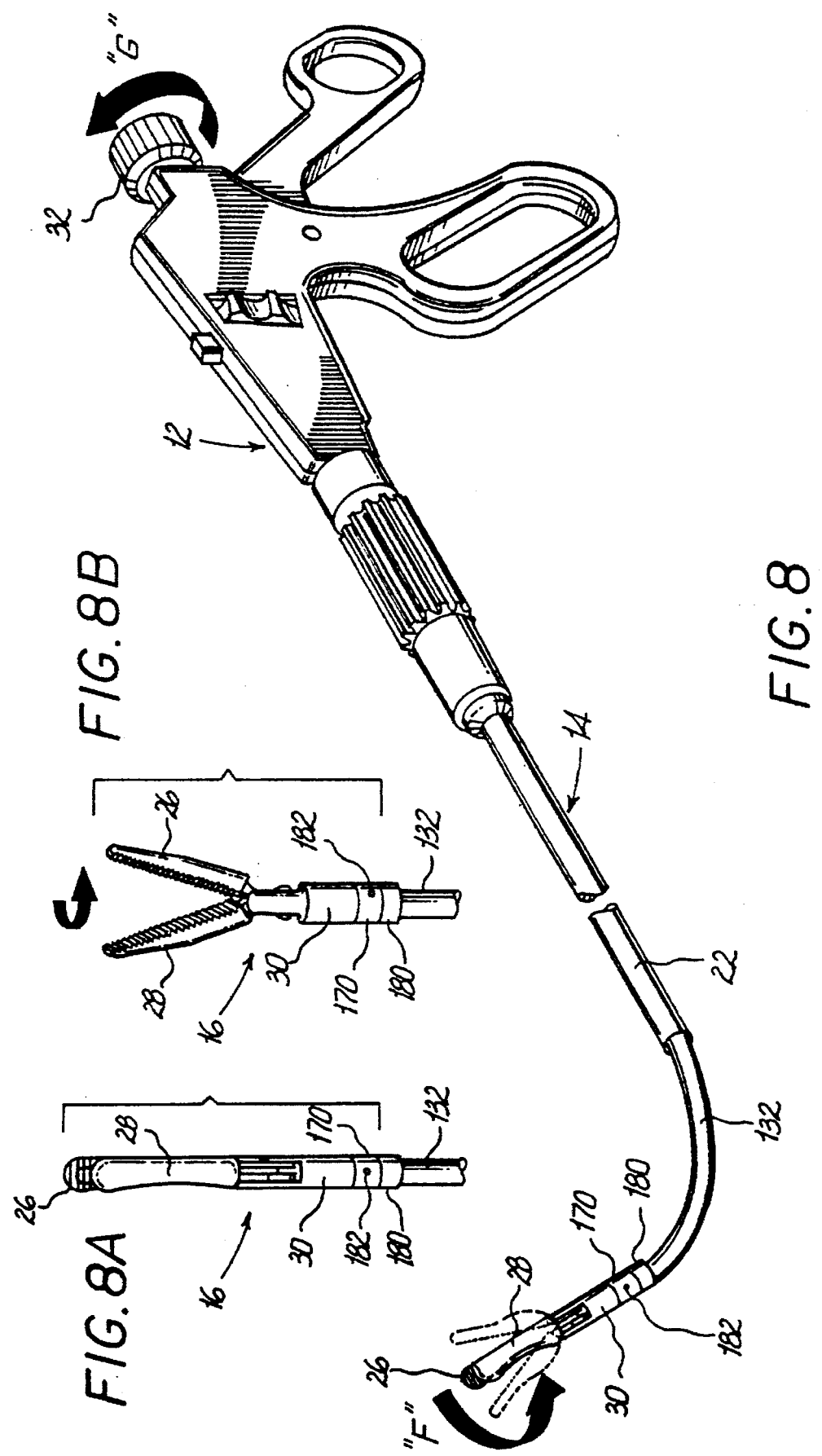
FIG. 8 is a perspective view of the needle driving apparatus of FIG. 1 illustrating the independent rotation of the needle holding jaws relative to the base of the needle holding assembly thereof.

Referring to FIG. 8, the independent rotation of the clevis member 30 together with the needle holding jaws 26 and 28 about an axis indicated by directional arrow "F" is achieved through the axial rotation of rotator knob 32 as indicated by directional arrow "G". As shown more clearly in FIGS. 8A and 8B, clevis member 30 together with jaw members 26 and 28, rotate relative to the base of the tool assembly 16 which is particularly defined by chuck member 170.

Figure 9:
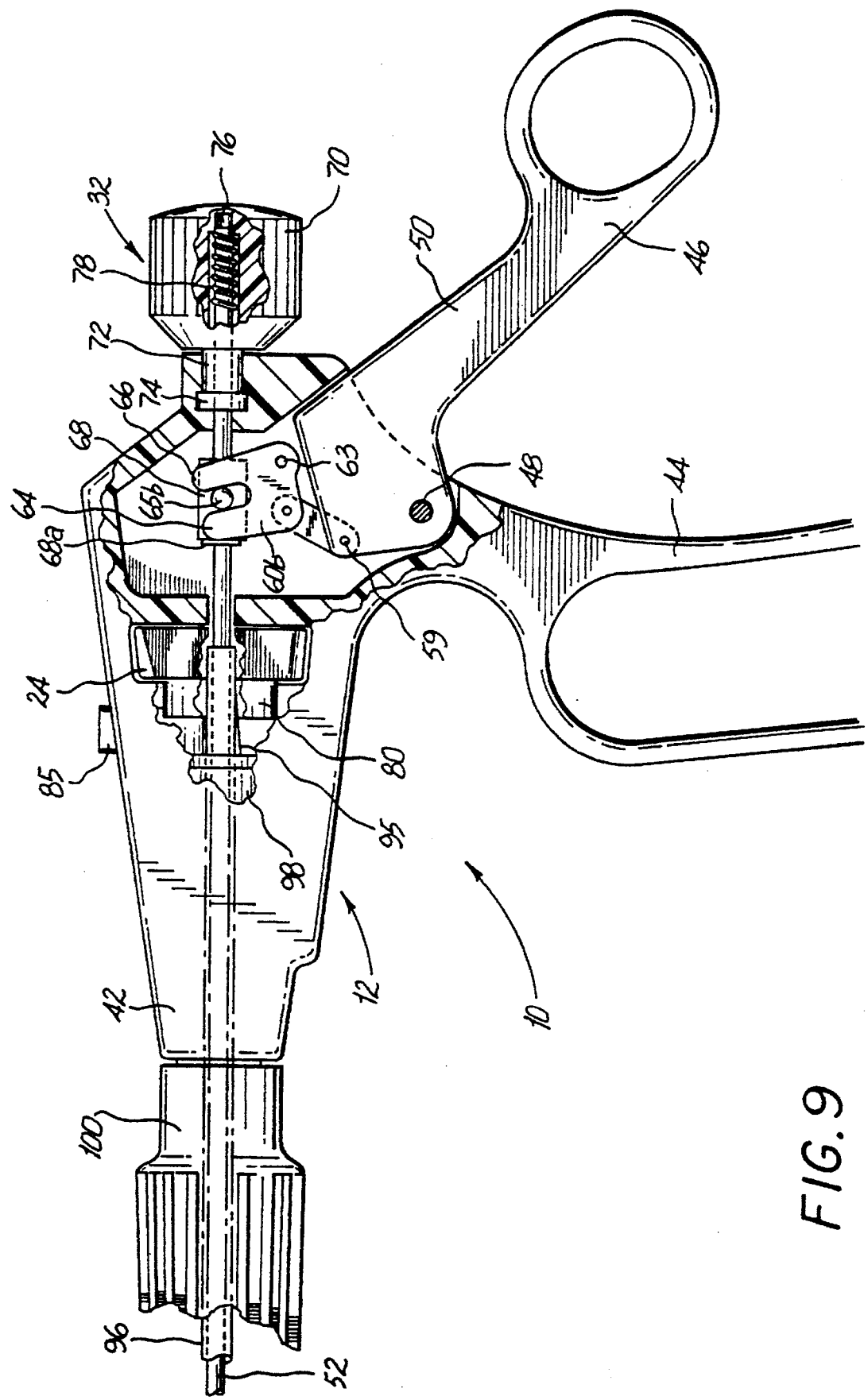
FIG. 9 is a side elevational view in partial cross-section of the handle assembly of the needle driving apparatus of FIG. 1.
Figure 10:
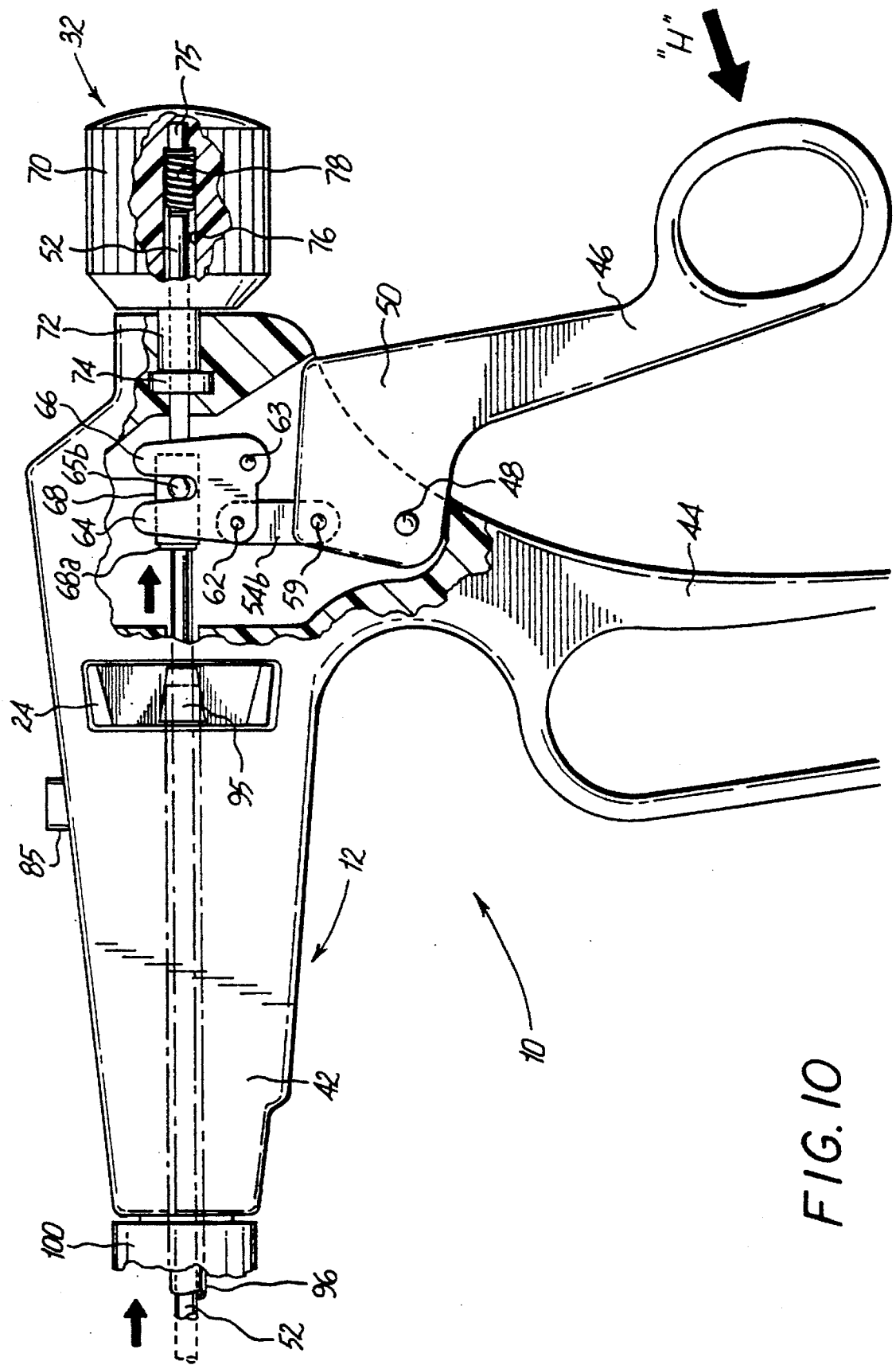
FIG. 10 is a side elevational view in partial cross-section of the handle assembly of the needle driving apparatus of FIG. 1 illustrating closure of the pivoting handle member thereof to effectuate cooperative movement of the needle holding jaws.

Referring now to FIGS. 9–11, in any of the operational positions described hereinabove, the needle holding jaws 26 and 28 of the surgical apparatus 10 of the subject invention may be moved between an open needle receiving position and a closed needle holding position through manipulation of the pivoting handle 46 of handle assembly 12. In particular, compression of pivoting handle in the direction indicated by arrow "H" in FIG. 10, will cause corresponding longitudinal movement of central control rod 52 in a proximal direction as forked engaging links 60a and 60b urge coupling block 68 rearwardly. Consequently, biasing spring 78 is compressed, storing energy to facilitate the forward return of control rod 52 upon the release of pivoting handle 46.

Turning to FIGS. 11 and 12, the proximal movement of central control rod 52 in response to manipulation of pivoting handle 46 results in the corresponding proximal translation of actuation wire 134 through a longitudinal distance indicated by "x". Thereupon, piston member 156 is drawn in a proximal direction through a corresponding longitudinal distance "x" within the tracked passageway 175 defined in clevis member 30, pulling therewith cam pin 166. As cam pin 166 translates from its distal-most position of FIG. 11 to its proximal-most position of FIG. 12, the cooperating jaw members 26 and 28 of tool assembly 16 are moved from a closed needle holding position to an open needle receiving position.

In sum, a novel surgical apparatus is provided for driving surgical needle during endoscopic or laparoscopic surgical procedures. The apparatus includes a first mechanism for effectuating the articulation of the needle holding assembly thereof relative to the endoscopic portion of the instrument, a second mechanism for effectuating the rotation of the needle holding assembly thereof relative to the endoscopic portion of the instrument, and a third mechanism for effectuating the independent rotation of the needle holding jaws relative to the base of the needle holding assembly thereof.

Although the endoscopic needle driving instrument of the subject invention has been described with respect to a preferred embodiment, it is apparent that changes or modifications may be made thereto without departing from the spirit or scope of the invention as defined by the appended claims. More specifically, the description of the jaw configuration of the tool assembly should not be construed to limit the present invention to an apparatus for use only in conjunction with needle driving procedures. To the contrary, it is believed that the tool assembly of the present invention may be configured in the form of any useful surgical tool including, for example, grasping jaws or biopsy forceps.

What is claimed is:

1. A surgical apparatus comprising:
   a) a handle assembly;
   b) a body portion extending from said handle assembly, defining a first longitudinal axis and including a resilient articulation portion;
   c) a tool assembly including a tool base portion defining a second longitudinal axis and a tool configured to rotate relative to, said tool base portion about said second longitudinal axis;
   d) said resilient articulation portion having a distal end portion which is movable between a first position wherein said second longitudinal axis of said tool base portion is substantially parallel to said first longitudinal axis of said body portion and a second position wherein said second longitudinal axis is substantially angularly disposed with respect to said first longitudinal axis to articulate said tool assembly, a proximal end portion of said tool base portion being fixedly and circumferentially mounted within said distal end portion of said resilient articulation portion;
   e) means for effectuating remote rotation of said tool assembly about the longitudinal axis of said body portion relative to said handle assembly;
   f) means for effectuating remote rotation of said tool relative to said tool base portion about said second longitudinal axis; and
   g) an axial drive screw assembly operatively associated with the handle assembly including a rotatable member and a longitudinally advancable member for effectuating movement of the distal end portion of the resilient articulation portion between said first position and said second position.

2. A surgical apparatus as recited in claim 1, wherein said tool comprises a pair of cooperating jaw members configured and adapted for use in remote suturing of tissue.

3. A surgical apparatus as recited in claim 2, further comprising actuation means extending from said handle assembly to said tool assembly for remotely moving said cooperating jaw members between an open position and a closed position.

4. A surgical apparatus as recited in claim 1, wherein said resilient articulation portion includes a resilient articulator tube having a preformed angular configuration and wherein said longitudinally advancable member comprises, an elongated cam tube axially movable with respect to said articulator tube, and wherein said axial drive screw assembly is configured to effectuate progressive movement of said cam tube relative to said articulator tube.

5. A surgical apparatus as recited in claim 4, wherein said resilient articulator tube is formed of a shape memory alloy.

6. A surgical apparatus as recited in claim 5, wherein said preformed angular configuration of said articulator tube is disposed at an angle of about 90° relative to said longitudinal axis of said body portion.

7. A surgical apparatus as recited in claim 1, wherein said means for rotating said tool assembly relative to said handle assembly comprises a rotation assembly including an axially rotatable dial member associated with said handle assembly, and an elongated rotation tube extending from said dial member, through said body portion, to said tool base portion.

8. A surgical apparatus as recited in claim 1, wherein said means for rotating said tool relative to said tool base portion comprises a rotator mechanism including an axially rotatable knob member associated with said handle assembly, and an elongated rotator rod extending from said knob member, through said body portion, to said tool.

9. A surgical apparatus as recited in claim 8, wherein said knob member is operatively disposed on a proximal end of said handle assembly.

10. A surgical apparatus as recited in claim 1, wherein said body portion is dimensioned and configured for endoscopic utilization.

11. A surgical apparatus comprising:
a) a handle assembly;
b) an elongated tubular body portion extending from said handle assembly, defining a first longitudinal axis and including a resilient articulation portion;
c) a tool assembly including a clevis member housing a pair of cooperating jaw members and a tool base portion defining a second longitudinal axis, said clevis member configured to rotate relative to said tool base portion about said second longitudinal axis;
d) actuation means for moving said cooperating jaw members between an open position and a closed position;
e) said resilient articulation portion having a distal end portion which is movable between a first position wherein said second longitudinal axis of said tool base portion is substantially parallel to said first longitudinal axis of said tubular body portion and a second position wherein said second longitudinal axis is angularly disposed with respect to said first longitudinal axis to articulate said tool assembly, a proximal end portion of said tool base portion being fixedly and circumferentially mounted within said distal end portion of said resilient articulation portion;
f) means for effectuating remote rotation of said tool assembly about said longitudinal axis of said tubular body portion relative to said handle assembly;
g) means for effectuating remote rotation of said clevis member relative to said tool base portion about said second longitudinal axis; and
h) an axial drive screw assembly operatively associated with the; handle assembly including a rotatable member and a longitudinally advancable member for effectuating movement of the distal end portion of the resilient articulation portion between said first position and said second position.

12. A surgical apparatus as recited in claim 11, wherein said resilient articulation portion includes a resilient articulator tube having a preformed angular configuration and wherein said longitudinally advancable member comprises, an elongated cam tube axially movable with respect to said articulator tube, and wherein said axial drive screw assembly is configured to effectuate progressive movement of said cam tube relative to said articulator tube.

13. A surgical apparatus as recited in claim 12, wherein said resilient articulator tube is formed of a shape memory alloy.

14. A surgical apparatus as recited in claim 13, wherein said preformed angular configuration of said articulator tube is disposed at an angle of about 90° relative to said longitudinal axis of said body portion.

15. A surgical apparatus as recited in claim 11, wherein said means for rotating said tool assembly relative to said handle assembly comprises a rotation assembly including an axially rotatable dial member associated with said handle assembly, and an elongated rotation tube extending from said dial member, through said tubular body portion, to said tool base portion.

16. A surgical apparatus as recited in claim 11, wherein said means for rotating said clevis member relative to said tool base portion comprises a rotator mechanism including an axially rotatable knob member associated with said handle assembly, and an elongated rotator rod extending from said knob member, through said tubular body portion, to said clevis member.

17. A surgical apparatus as recited in claim 11, wherein said tubular body portion is dimensioned and configured for endoscopic utilization.

18. A surgical apparatus comprising:
a) a handle assembly;
b) a tubular body portion extending from said handle assembly, defining a first longitudinal axis and including a resilient articulation portion;
c) a tool assembly associated with a distal end portion of said resilient articulation portion, said tool assembly including a clevis member housing a pair of cooperating jaws and a tool base portion defining a second longitudinal axis and adapted to permit relative rotation of said clevis member with respect thereto;
d) actuation means extending from said handle assembly to said tool assembly for moving said cooperating jaws between an open position and a closed position;
e) said distal end portion of said resilient articulation portion being movable between a first position wherein said second longitudinal axis of said tool base portion is substantially parallel to said first longitudinal axis of said tubular body portion and a second position wherein said second longitudinal axis is substantially angularly disposed with respect to said first longitudinal axis to progressively articulate said tool assembly, a proximal end portion of said tool base portion being fixedly and circumferentially mounted within said distal end portion of said resilient articulation portion;
f) means for effectuating remote rotation of said tool assembly about said longitudinal axis of said tubular body portion relative to said handle assembly;
g) means for effectuating remote rotation of said clevis member and said jaws relative to said tool base portion about said second longitudinal axis; and
h) an axial drive screw assembly operatively associated with handle assembly including a rotatable member and a longitudinally advancable member for effectuating movement of the distal end portion of the resilient articulation portion between said first position and said second position.

19. A surgical apparatus as recited in claim 18, wherein said resilient articulation portion includes a resilient articulator tube having a preformed angular configuration and wherein said longitudinally advancable member comprises, an elongated cam tube axially movable with respect to said articulator tube, and wherein said axial drive screw assembly is configured to effectuate progressive movement of said cam tube relative to said articulator tube.

20. A surgical apparatus as recited in claim 19, wherein said resilient articulator tube is formed of a shape memory alloy.

21. A surgical apparatus as recited in claim 20, wherein said preformed angular configuration of said articulator tube is disposed at an angle of about 90° relative to said longitudinal axis of said body portion.

22. A surgical apparatus as recited in claim 18, wherein said means for rotating said tool assembly relative to said handle assembly comprises a rotation assembly including an axially rotatable dial member associated with said handle assembly, and an elongated rotation tube extending from said dial member, through said tubular body portion, to said tool base portion.

23. A surgical apparatus as recited in claim 18, wherein said means for rotating said clevis member relative to said tool base portion comprises a rotator mechanism including an axially rotatable knob member associated with said handle assembly, and an elongated rotator rod extending from said knob member, through said tubular body portion, to said clevis member.

24. A surgical apparatus as recited in claim 18, wherein said tubular body portion is dimensioned and configured for endoscopic utilization.

* * * * *